United States Patent
Tang et al.

(10) Patent No.: US 10,703,845 B2
(45) Date of Patent: Jul. 7, 2020

(54) PREPARATION OF MALEATE AND MALEIMIDE MONOMERS AND POLYMERIC MATERIALS FROM TRIGLYCERIDES

(71) Applicant: University of South Carolina, Columbia, SC (US)

(72) Inventors: Chuanbing Tang, Columbia, SC (US); Liang Yuan, Columbia, SC (US); Meghan Lamm, Columbia, SC (US)

(73) Assignee: University of South Carolina, Columbia, SC (US)

( * ) Notice: Subject to any disclaimer, the term of this patent is extended or adjusted under 35 U.S.C. 154(b) by 151 days.

(21) Appl. No.: 15/812,157

(22) Filed: Nov. 14, 2017

(65) Prior Publication Data

US 2018/0134829 A1 May 17, 2018

Related U.S. Application Data (60) Provisional application No. 62/422,753, filed on Nov. 16, 2016.

(51) Int. Cl.

| | | |
|---|---|---|
| C08F 222/40 | (2006.01) | |
| C07D 207/452 | (2006.01) | |
| C07C 233/20 | (2006.01) | |
| C07C 29/136 | (2006.01) | |
| C07C 231/02 | (2006.01) | |
| C08F 222/22 | (2006.01) | |

(52) U.S. Cl.
CPC .......... *C08F 222/40* (2013.01); *C07C 29/136* (2013.01); *C07C 231/02* (2013.01); *C07C 233/20* (2013.01); *C07D 207/452* (2013.01); *C08F 222/22* (2013.01); *C08F 222/225* (2020.02); *C08F 222/406* (2020.02)

(58) Field of Classification Search
None
See application file for complete search history.

(56) References Cited

PUBLICATIONS

Gandini A. Polymers from renewable resources: a challenge for the future of macromolecular materials. Macromolecules 2008;41:9491-504.
Yu L, Dean K, Li L. Polymer blends and composites from renewable resources. Progress in polymer science 2006;31:576-602.
Xia Y, Larock RC. Plant oil-based polymeric materials: synthesis, properties, and applications. Green Chemistry 2010;12:1893-909.
Williams CK, Hillmyer MA. Polymers from renewable resources: a perspective for a special issue of polymer reviews. Polymer reviews 2008;48:1-10.
Luo Q, Liu M, Xu Y, Ionescu M, Petrovic ZS. Thermosetting allyl resins derived from soybean oil. Macromolecules 2011;44:7149-57.
Li F, Hanson M, Larock R. Soybean oil-divinylbenzene thermosetting polymers: synthesis, structure, properties and their relationships. Polymer 2001;42:1567-79.
Li F, Larock RC. New soybean oil-styrene-divinylbenzene thermosetting copolymers. I. Synthesis and characterization. Journal of applied polymer science 2001;80:658-70.
Larock RC, Dong X, Chung S, Reddy CK, Ehlers LE. Preparation of conjugated soybean oil and other natural oils and fatty acids by homogeneous transition metal catalysis. Journal of the American Oil Chemists' Society 2001;78:447-53.
Campanella A, Baltanas M, Capel-Sanchez M, Campos-Martin J, Fierro J. Soybean oil epoxidation with hydrogen peroxide using an amorphous Ti/SiO 2 catalyst. Green Chemistry 2004;6:330-34.
Guo A, Demydov D, Zhang W, Petrovic ZS. Polyols and polyurethanes from hydroformylation of soybean oil. Journal of Polymers and the Environment 2002;10:49-52.
Refvik M, Larock R, Tian Q. Ruthenium-catalyzed metathesis of plant oils. Journal of the American Oil Chemists' Society 1999;76:93-98.
King J, Holliday R, List G. Hydrolysis of soybean oil in a subcritical water flow reactor. Green Chemistry 1999;1:261-64.
Liu X, He H, Wang Y, Zhu S, Piao X. Transesterification of soybean oil to biodiesel using CaO as a solid base catalyst. Fuel 2008;87:216-21.
Huang H, Hoogenboom R, Leenen MA, Guillet P, Jonas AM, Schubert US, Gohy JF. Solvent-induced morphological transition in core-cross-linked block copolymer micelles. Journal of the American Chemical Society 2006; 128: 3784-3788.
Chernykh A, Alam S, Jayasooriya A A, Bahr J, Chisholm BJ. Living carbocationic polymerization of a vinyl ether monomer derived from soybean oil, 2-(vinyloxy) ethyl soyate. Green Chemistry. 2013;15:1834-8.
Yuan L, Wang Z, Trenor NM, Tang C. Robust Amidation Transformation of Plant Oils into Fatty Derivatives for Sustainable Monomers and Polymers. Macromolecules 2015; 48: 1320-1328.
Yuan L, Wang Z, Trenor NM, Tang C. Amidation of triglycerides by amino alcohols and their impact on plant oil-derived polymers. Polymer Chemistry 2016; 7: 2790-2798.

*Primary Examiner* — Kamal A Saeed
(74) *Attorney, Agent, or Firm* — Dority & Manning, P.A.

(57) ABSTRACT

Monomer compounds and methods of synthesizing monomer compounds are disclosed. The monomer compounds can include maleate and maleimide monomers having fatty acid moieties. The monomer compounds can be derived from renewable sources such as corn, soybean, and sunflower oils. The monomer compounds can be formed into homopolymers as well as copolymers. The copolymers can include petroleum-derived monomers such as styrene, ethylene, and propylene.

12 Claims, 7 Drawing Sheets

PREPARATION OF MALEATE AND MALEIMIDE MONOMERS AND POLYMERIC MATERIALS FROM TRIGLYCERIDES

CROSS-REFERENCE TO A RELATED APPLICATION

The present application claims priority to U.S. Provisional Patent Application Ser. No. 62/422,753 titled "PREPARATION OF MALEATE AND MALEIMIDE MONOMERS AND POLYMERIC MATERIALS FROM TRIGLYCERIDES" of Tang, et al. filed on Nov. 16, 2016, the disclosure of which is incorporated by reference herein.

BACKGROUND OF THE INVENTION

There is continued interest in the development of environmentally-friendly polymeric materials derived from renewable resources. For one, there is a concern about the cost of and the depletion of petroleum resources. Perhaps more importantly, plastic waste from consumers and industry has become a major problem. Petroleum-derived plastics are filling up our landfills and collecting in our oceans and other water bodies. All sorts of wildlife are known to consume plastic particles and become entangled in plastic materials, causing injury to their health and even death. Furthermore, plastics and their constituent chemicals can be ingested by humans as the plastics make their way through the food chain.

Unfortunately, there have been challenges in developing environmentally-friendly polymers having properties suitable for replacing petroleum-derived plastics. One challenge is the lack of synthetic strategies to convert renewable resources to monomers that can be polymerized. A second challenge is the need for polymerization techniques that do not affect un saturated double bonds and other functional groups during polymerization. The teachings of the present disclosure seek to improve on the prior art by addressing these and other challenges.

BRIEF SUMMARY OF THE INVENTION

Embodiments of the present disclosure include monomer compounds and methods of synthesizing monomer compounds. More specifically, embodiments of the present disclosure include maleate and maleimide monomers having fatty acid moieties as well as synthesis methods thereof. Embodiments also include polymers and copolymers having maleate and maleimide monomers with fatty acid moieties.

The polymeric materials disclosed herein have the potential to replace polymers made from petroleum chemicals, thus reducing the dependence on non-renewable fossil fuels. The deleterious effects that petroleum-derived plastics have on the environment may also be reduced. Specifically, polymers according to the present disclosure may have increased biodegradability and reduced toxicity relative to traditional petroleum-based polymers.

Monomers of the present invention can include aliphatic carbon chains derived from triglycerides. Triglycerides make good candidates as the building blocks of polymeric materials due to their natural abundance and inherent functionality, like the unsaturated double bonds and ester groups. However, there are many challenges in producing polymers using fatty acids due to their heterogeneous and non-uniform structures.

As discussed above, challenges in the art include a lack of synthetic strategies to convert triglycerides such as plant oils to polymerizable monomers, as well as deriving polymerization techniques that do not affect the unsaturated double bonds in the fatty acids. This also limits the possibility of substituting petroleum based polymers with bio-renewable polymers in the areas of thermoplastic elastomers, thermoplastic resins, polymeric wax, varnishes, coatings, and other applications.

The present disclosure teaches the production of monomers from triglycerides. These monomers can contain polymerizable oxazoline groups, vinyl ether groups, norbornene groups, or (meth)acrylate groups. These functional groups can allow for increased opportunities for use in copolymers and provide avenues for obtaining beneficial properties directed at specific applications.

DETAILED DESCRIPTION OF THE INVENTION

Embodiments of the present disclosure include monomer compounds and methods of synthesizing monomer compounds. More specifically, embodiments of the present disclosure include maleate and maleimide monomers having fatty acid moieties. Embodiments also include polymers derived from maleate and maleimide monomers with fatty acid moieties.

The present disclosure includes methods for the preparation of monomers and polymers from renewable triglycerides. Monomers can be developed in the form of maleates and N-substituted maleimides. Polymers can include copolymers that feature maleates and maleimides. Applications of the disclosed monomers and polymers include thermoplastics, fibers, films, insulation, coating formulations, and emulsion latex. Triglyceride-derived fatty acid polymers of the present disclosure can be particularly advantageous for medical applications such as sutures due their biodegradability and low toxicity.

Efficient methods for the development of monomers from triglycerides are provided. The monomers can be polymerized through several different methods. Polymers with the morphology of linear homo-polymers, random copolymers, block copolymers, multi-graft copolymers, and polymer composites can be prepared. The copolymers can include monomers derived from triglycerides in combination with other monomers such as styrene, isocyanates, acids, acrylates, and methacrylates.

The maleate and maleimide monomers can be prepared from mono-hydroxyl group or mono-amine group containing derivatives of plant oils. Homo-polymers, random copolymers, block copolymers, graft copolymers, and composites can contain at least one polymerized monomer derived from triglycerides. Polymers based on triglyceride-derived monomers can be prepared through atom transfer radical polymerization (ATRP), radical addition fragmentation transfer polymerization (RAFT), nitroxide mediated polymerization (NMP), free radical polymerization, controlled radical polymerization, living radical polymerization, and emulsion polymerization. In some embodiments, random copolymers, block copolymers, graft copolymers, emulsions, and composites can bear other monomer units selected from olefins, methacrylates, acrylates, styrenes, acrylamides, acrylonitriles and other functional monomer units.

Figure 1:
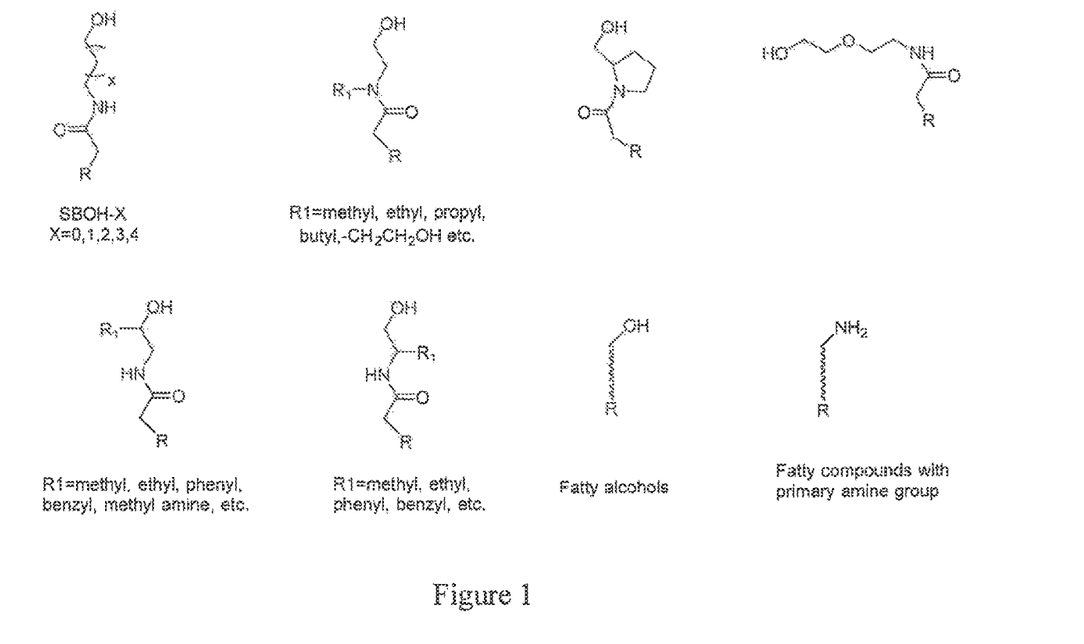
FIG. 1 shows hydroxyl group and primary amine group containing fatty compounds derived from plant oils.
Figure 2:
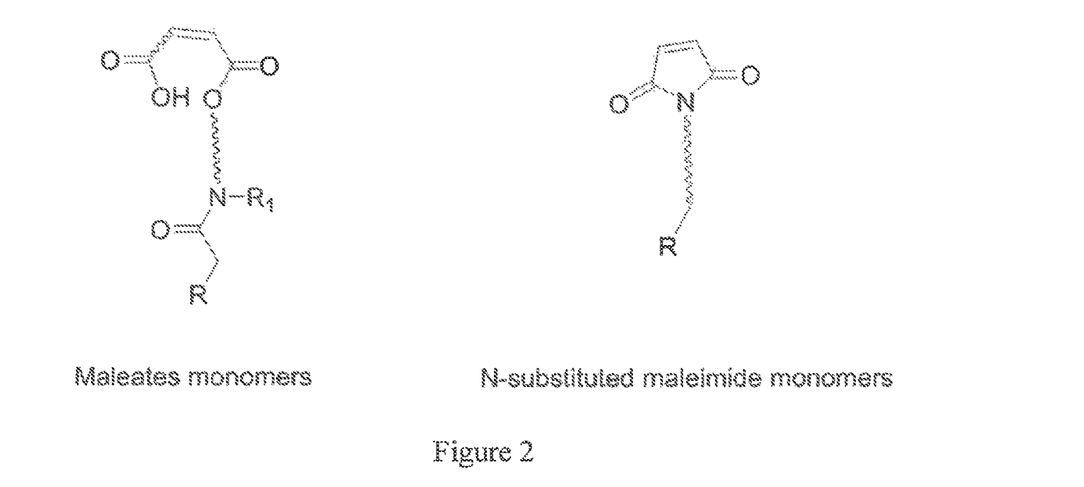
FIG. 2 shows maleates and N-substituted maleimide monomers of the present disclosure.

Embodiments include maleate and N-substituted maleimide monomers derived from plant oils. The monomers can be polymerized to form homopolymers, or copolymerized with other monomers such as peteroleum-derived monomers. The ester groups in the triglycerides can be completely converted to glycerol and functionalized fatty acids (e.g., mono-hydroxyl fatty amides, or primary amine containing compounds, as shown in FIG. 1). The double bonds in the alkyl chains of fatty acid group containing compounds can be epoxidized. The hydroxyl group or amine group containing compounds (with a double bond or epoxy group) can be used for making mono-functional monomers of maleates and N-substituted maleimides as seen in FIG. 2.

The methods and monomers discussed can have multiple advantageous features. For example, maleate and N-substituted maleimide monomers can be derived from fatty acids with double bonds or epoxidized double bonds in the alkyl chain. The triglycerides-based maleate and N-substituted maleimide monomers can be made into homopolymers, copolymers, random copolymers, and block copolymers. Copolymers with multiple components (AB diblock copolymers, AB random copolymers, ABA triblock copolymers, ABC random copolymers, ABC block copolymers, etc.) can be produced from bulk, solution, and emulsion polymerization. Specific copolymers that can be produced include poly(styrene-co-maleate), poly(styrene-co-maleate-co-vinyl acetate), poly(methyl methacrylate-co-maleate), poly(styrene-co-maleimide), and poly(styrene-co-maleimide-co-vinyl acetate).

Graft copolymers can be produced from a polymer backbone and macro-initiators derived from an organic substrate such as lignin, cellulose, and chitin. Graft copolymers can also be produced having a multi-functional core to make star-shaped copolymers. Graft copolymers can also be produced from a modified inorganic substrate such as silicon nanoparticles, carbon nanotubes, clay, titanium nanoparticles, gold nanoparticles, quantum dots, and polyhedral oligomeric silsesquioxanes (POSS).

Figure 3:
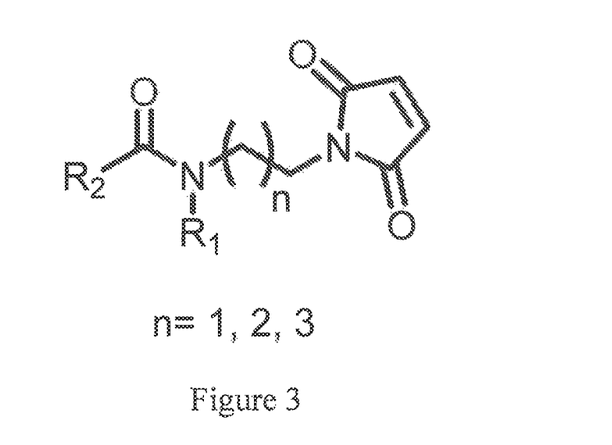
FIG. 3 shows a generic N-substituted maleimide monomer of the present disclosure.

FIG. 3 shows a generic N-substituted maleimide monomer of the present disclosure. The number of carbons between each of the nitrogen atoms can range from two to four, with n equaling 1, 2, or 3. The $R_1$ group can also be controlled and can be a hydrogen atom as well as methyl, ethyl, propyl, and butyl groups. The $R_2$ group represents an aliphatic chain from a fatty acid. The fatty acid chains can be derived from triglyerides and can include oleic acid, linolenic acid, linoleic acid, stearic acid, palmitic acid, and erucic acid. However, other fatty acids can be used to provide different aliphatic chains. The fatty acids can be derived from soybean, sunflower, safflower, rapeseed, olive, castor, and peanut oils, for example.

Figure 4:
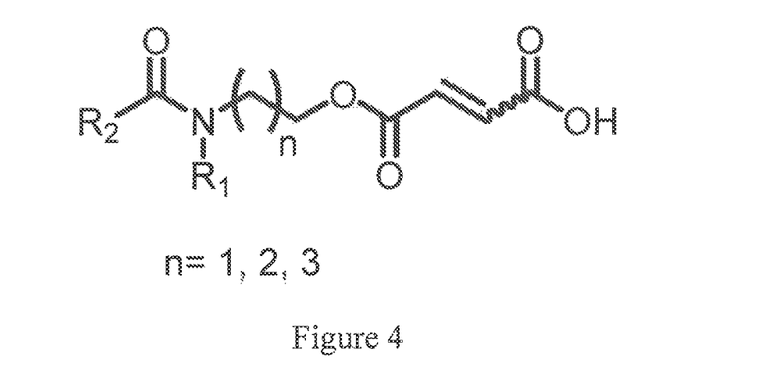
FIG. 4 shows a generic maleate monomer of the present disclosure.

FIG. 4 shows a generic maleate monomer of the present disclosure. Similar to the maleimide monomers, the number of carbons between each of the nitrogen atoms can range from two to four, with n equaling 1, 2, or 3. The $R_1$ group can be controlled and can be a hydrogen atom as well as methyl, ethyl, propyl, and butyl groups. The $R_2$ group represents an aliphatic chain from a fatty acid. The fatty acids chains can vary and include all of those discussed with regard to the malelimide monomer of FIG. 3.

Figure 5:
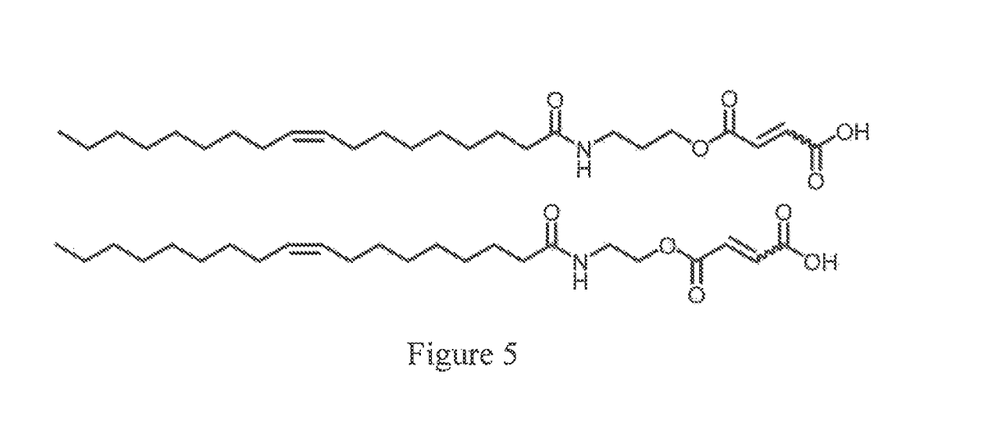
FIG. 5 shows two maleate monomers having different linking groups (the top with a 3-carbon linking group and the bottom with a 2-carbon linking group).
Figure 6:
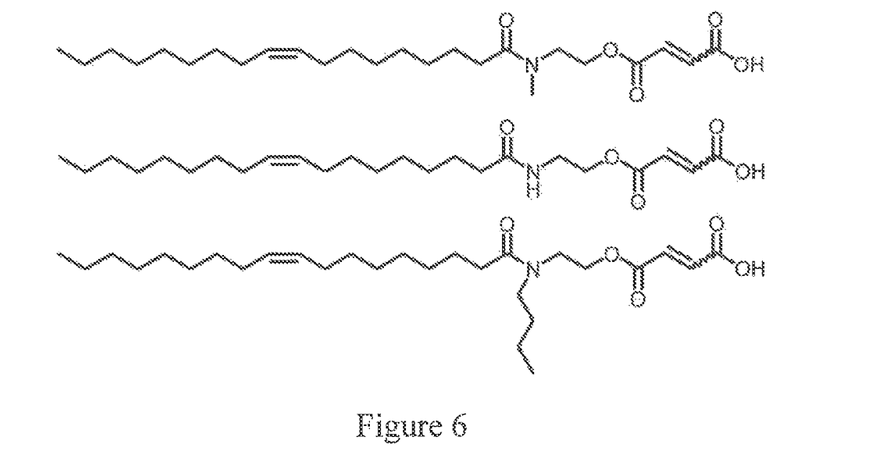
FIG. 6 shows maleate monomers featuring various $R_1$ groups.

FIG. 5 shows two maleate monomers having different linking groups, the top with a 3-carbon linking group and the bottom with a 2-carbon linking group. The maleate monomers of FIG. 5 are formed with the aliphatic chain of oleic acid. FIG. 6 shows maleate monomers featuring various $R_1$ groups. From top to bottom, the $R_1$ groups of the maleate monomers are a methyl group, followed by a hydrogen atom, followed by a butyl group.

Figure 7:
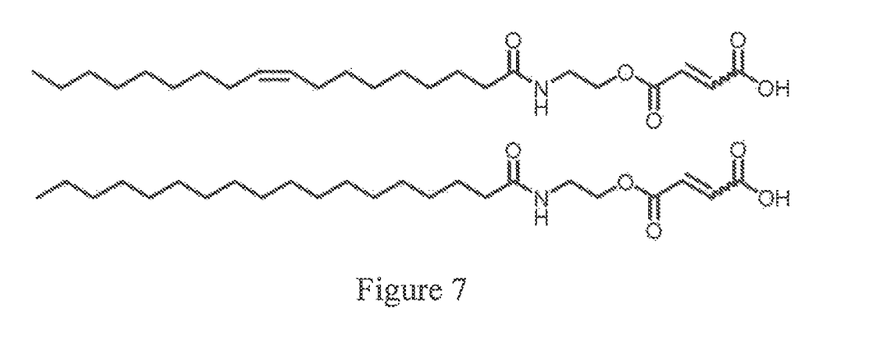
FIG. 7 shows maleate monomers featuring various $R_2$ groups.

FIG. 7 shows maleate monomers featuring various $R_2$ groups. The top of FIG. 7 shows a maleate monomer having an oleic acid aliphatic carbon chain serving as the $R_2$ group. The bottom of FIG. 7 shows a maleate monomer having a stearic acid aliphatic carbon chain serving as the $R_2$ group.

Figure 8:
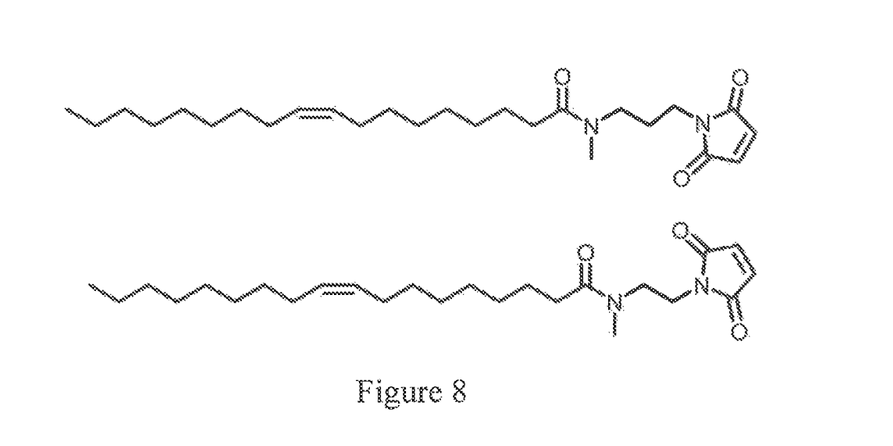
FIG. 8 shows N-substituted maleimide monomers featuring different linking groups (the top with a 3-carbon linking group and the bottom with a 2-carbon linking group).

FIG. 8 shows N-substituted maleimide monomers featuring different linking groups. The top of FIG. 8 shows a 3-carbon linking group and the bottom shows a 2-carbon linking group. Both N-substituted maleimide monomers of FIG. 8 are shown having an oleic acid aliphatic carbon chain serving as the $R_2$ group.

Figure 9:
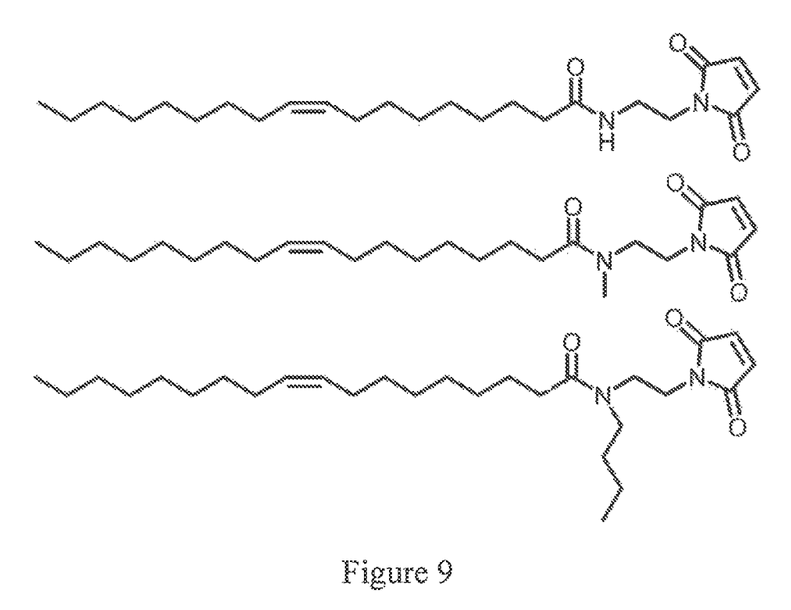
FIG. 9 shows N-substituted maleimide monomers featuring different $R_1$ groups.

FIG. 9 shows N-substituted maleimide monomers featuring different $R_1$ groups. From top to bottom, the $R_1$ groups of the maleimide monomers are a hydrogen atom, followed by a methyl group, followed by butyl group.

Figure 10:
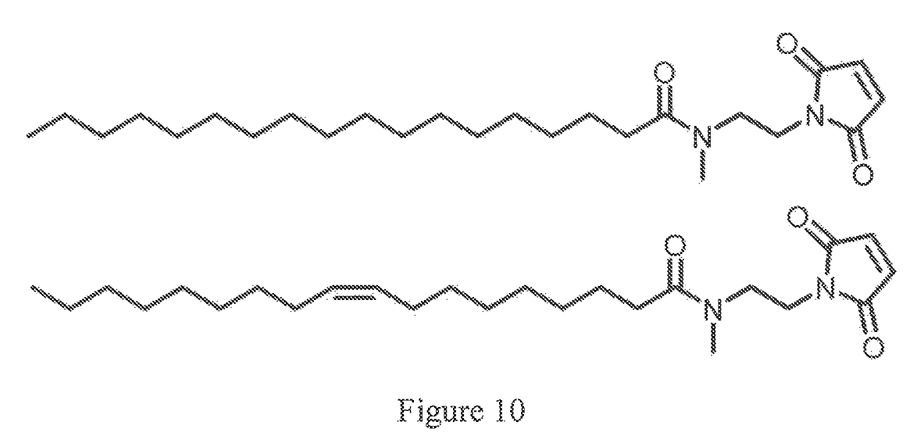
FIG. 10 shows N-substituted maleimide monomers featuring different $R_2$ groups.

FIG. 10 shows N-substituted maleimide monomers featuring different $R_2$ groups. The top of FIG. 10 shows a maleimide monomer having a stearic acid aliphatic carbon chain serving as the $R_2$ group. The bottom of FIG. 10 shows a maleimide monomer having an oleic acid aliphatic carbon chain serving as the $R_2$ group.

Figure 11:
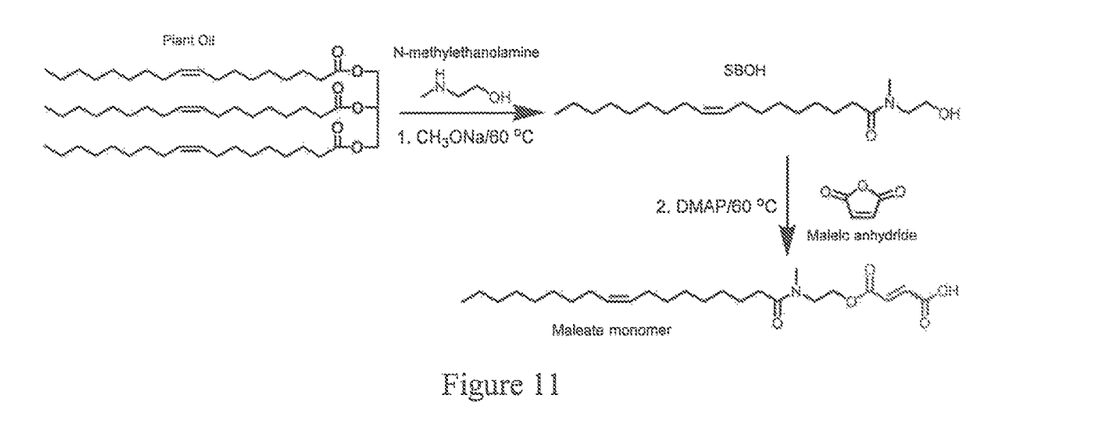
FIG. 11 shows a synthesis method for producing maleate monomers.
Figure 12:
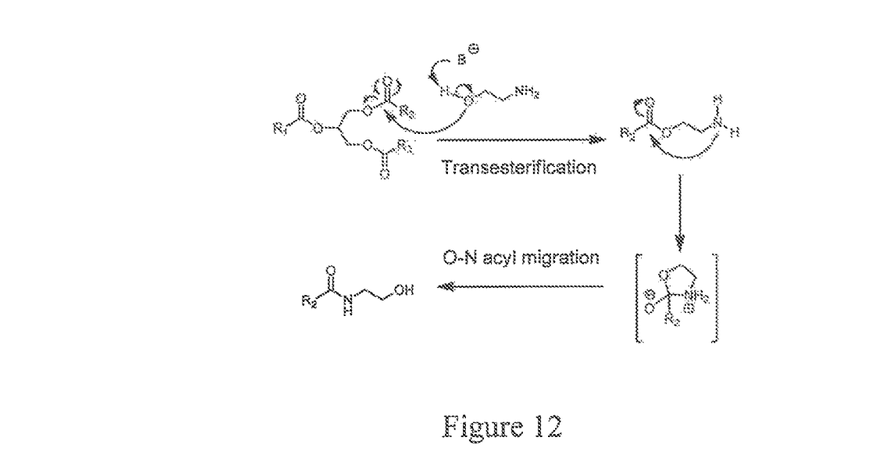
FIG. 12 shows a base-catalyzed transesterification reaction mechanism for producing a fatty alcohol of having a primary amine group.

FIG. 11 shows a synthesis method for producing maleate monomers. Plant oil triglycerides can be transformed into fatty acid alcohols. A similar synthesis using diaminoethylene, preferably in excess, can be used to obtain fatty components having primary amine groups (SBPA). The plant oil can be heated under nitrogen for 1 hour at 100° C. After cooling, N-methylethanolamine and sodium methoxide can be added. The solution can then be heated again (e.g., to 60° C.) and the reaction allowed to complete. Methylene chloride can then be added and the mixture can be washed with brine. Finally, the resulting organic layer can be dried using magnesium sulfate or another drying agent and the solvent can be removed under reduced pressure. FIG. 12 shows a base-catalyzed transesterification mechanism for producing a fatty alcohol having an initial primary amine group, resulting in a secondary amide.

Figure 13:
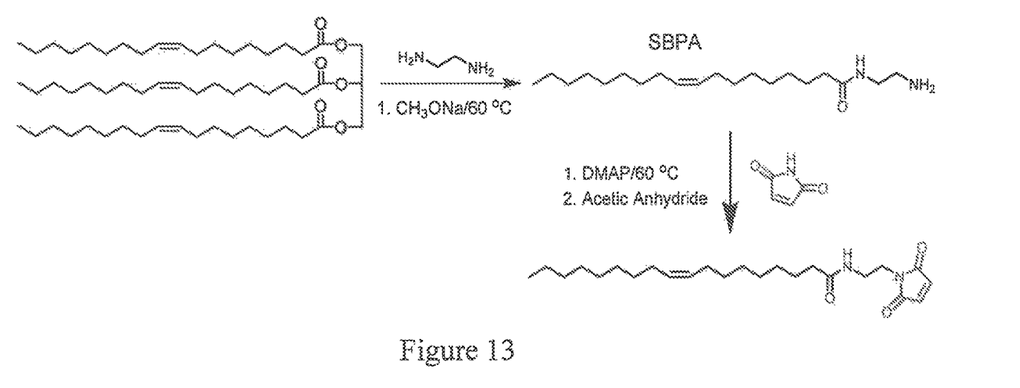
FIG. 13 shows a synthesis method for maleimide monomers.

FIG. 13 shows a synthesis method for N-substituted maleimide monomers. The synthesis of N-substituted maleimide monomers is shown involving two steps. First, there is conversion of plant oils to a fatty acid having a primary amine group using a base-catalyzed transesterification. Second, there is conversion of the fatty acid having a primary amine group to an N-substituted maleimide monomer using a subsequent base-catalyzed transesterification followed by a dehydration-cyclization reaction.

Figure 14:
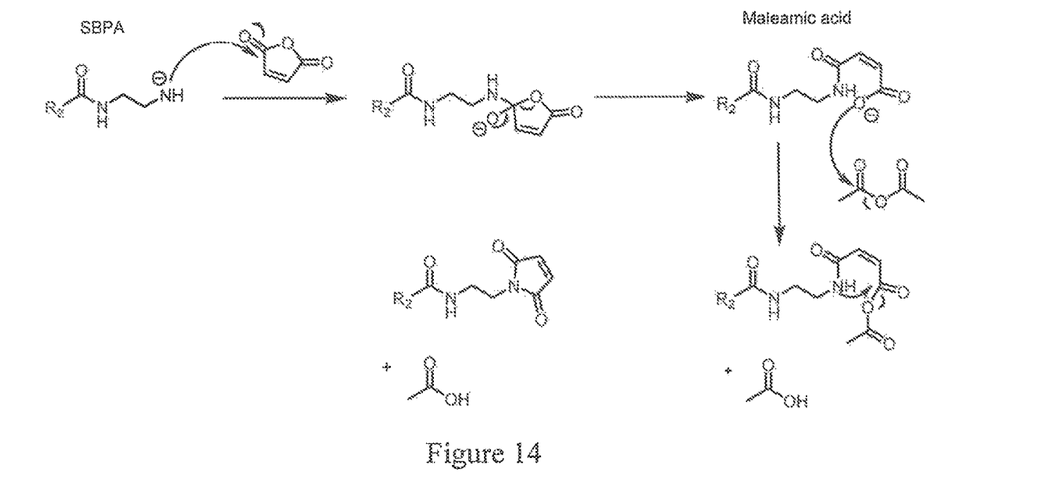
FIG. 14 shows a reaction mechanism for producing N-substituted maleimide monomers.

More specifically, a fatty acid having a primary amine group and maleimide can be mixed and heated (e.g., to 60° C.). After conversion to the N-substituted maleamic acid product, acetic anhydride can be added and the mixture stirred. The product can be taken up in an organic solvent (e.g., DCM) and washed subsequently with sodium bicarbonate and brine, multiple times if desired. Finally, the organic layer can be dried with magnesium sulfate and the solvent can be removed under reduced pressure. FIG. 13 illustrates this synthesis method and FIG. 14 illustrates the reaction mechanism for the transesterification and dehydration-cyclization conversion of the fatty alcohol having a primary amine to the N-substituted maleimide monomer.

Multiple different but equivalent synthesis steps are possible including variations in the amino alcohol or diamine reagent. These steps would result in slightly different structures. A variety of different plant oils, discussed above, as well as different bases can be used. Alternative or additional suitable bases include solid-supported catalysts, inorganic bases (e.g., potassium carbonate), and organic bases (e.g., triethylamine).

Figure 15:
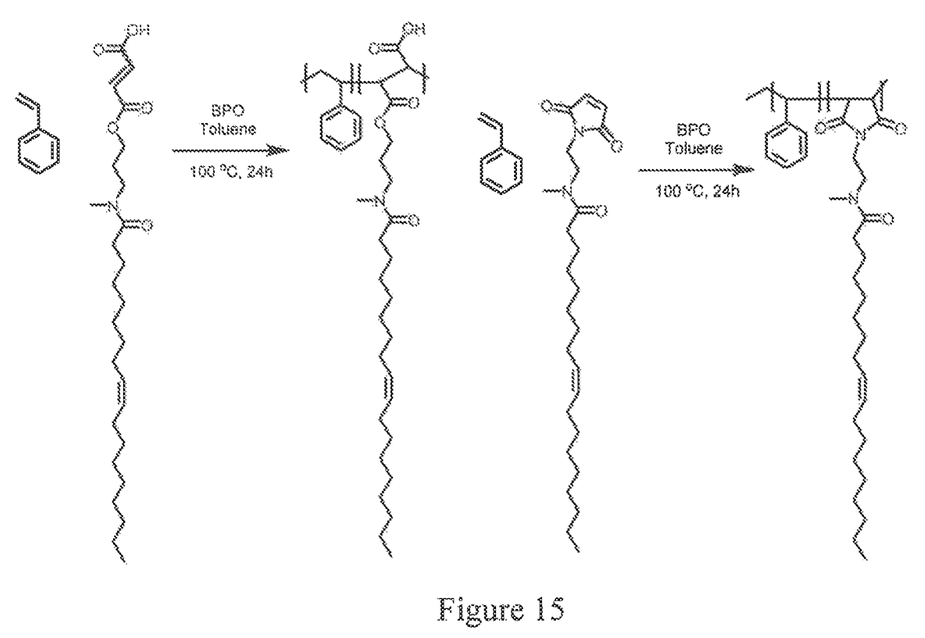
FIG. 15 shows polymerization of maleate (left) and maleimide (right) with styrene.

FIG. 15 illustrates free-radical copolymerization of maleate (left) and maleimide monomers (right) with styrene. However, the reaction can be customized to synthesize other types of copolymers besides styrene (e.g., olefins, methacrylates, acrylates, styrenes, acrylamides, acrylonitriles, etc.), as discussed above.

Soy maleate and styrene can be dissolved in a dry solvent such as toluene and mixed. Benzoyl peroxide can then be added. The mixture can then be sealed and purged with nitrogen. After purging, the mixture can be heated to drive the polymerization reaction. The polymer can then be precipitated in, for example, cold methanol. The mixture can then be dried to obtain the polymer product. Table 1 shows some general properties of maleate copolymers of the present invention.

TABLE 1

Characterization of a variety of maleate containing polymers.

| Polymer | Mn (g/mol) | Đ | $T_g$ (° C.) | Polymer Physical Description |
| --- | --- | --- | --- | --- |
| Poly(styrene-co-soy maleate) | 18400 | 1.90 | 58 | Brittle solid |
| Poly(MMA-co-soy maleate) | 11100 | 1.37 | 83 | Powder |
| Poly(styrene-co-soy maleate-co-BA) | 10300 | 1.28 | 19 | Flaky solid |

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Maleate monomers were prepared using mono-hydroxyl group containing fatty compounds as shown in FIG. 1. The fatty compounds (1.0 mol) and maleic anhydride (1.0 mol) were put together in a 1 L round bottomed flask. A catalyst (DMAP) was added to the mixture before the mixture was heated (to approximately 80° C.) to promote the esterification reaction. However, the reaction can also be driven at high temperatures without a catalyst. Conversion of both reactants was driven near completion to produce the maleate monomer. Monomers with different structures can be prepared with varied mono-hydroxyl containing fatty compounds, as given in FIG. 1.

Example 2

Copolymers from maleate monomers of Example 1 were prepared by free radical polymerization, which can be carried out in bulk, solution, or emulsion. A soy-based maleate monomer (4.0 g, 9.15 mmol), styrene (0.5 g, 4.8 mmol) and benzoyl peroxide (28 mg, 0.09 mmol) were dissolved together in 9 ml toluene. After purging with nitrogen for 20 minutes, the solution was put in a 100° C. oil bath to start the polymerization and left at this temperature for 16 hours. The product was precipitated using methanol and dried under vacuum. The co-monomers could also have been chosen from other types of monomers, including acrylates, methacrylates, etc. (as discussed above).

Example 3

Preparation of N-substituted maleimide monomers of FIG. 2 was demonstrated. A plant oil derived compound with a primary amine group (1.0 mol) and maleic anhydride (1.0 mol) were mixed together in a round bottomed flask with a suitable solvent. N-substituted maleamic acid product was formed. The conversion of N-substituted maleamic acid to the N-substituted maleimide monomers was obtained after a dehydration-cyclization reaction in the presence of a dehydration catalyst or dehydration agent, such as acetic anhydride, or EDC.

Example 4

Polymerization of maleimide monomers from Example 3 was demonstrated. These monomers can be homopolymerized or copolymerized with other monomers by free radical polymerization in bulk, solution, or emulsion. An N-substituted maleimide monomer with soy chains (1.0 g), styrene (1.0 g), and azobisisobutyronitrile (AIBN, 10 mg) were mixed in 2.0 ml toluene. The solution was purged with nitrogen and put into an oil bath at 70° C. After 10 hours, the polymer product was precipitated from cold methanol and dried under vacuum.

Example 5

The following is a representative synthesis for the fatty alcohols and/or fatty components containing primary amine groups (SBPA). A similar synthesis using diaminoethylene, preferably in excess, can be used to obtain fatty components having primary amine groups (SBPA).

Plant oil (25 g, containing 0.086 moles ester groups) was purged at 100° C. for 1 hour under nitrogen in a 500 mL RBF (round-bottom flask). After cooling, N-methylethanolamine (6.54 g, 0.106 moles) and sodium methoxide (0.49 mL, 0.0026 moles) were added. The solution was placed in a 60° C. oil bath and allowed to react to completion (~4 h). Methylene chloride (10 mL) was added and the mixture was washed three times with brine. Finally, the resulting organic layer was dried using magnesium sulfate and the solvent was removed under reduced pressure. The reaction can be seen in the top portion of FIG. 11. FIG. 12 shows the base-catalyzed transesterification mechanism for producing a fatty alcohol of having a primary amine group.

Example 6

The following is a representative synthesis for N-substituted maleimide monomers. A fatty acid having a primary amine group (43.7 g, 0.1 mole) and maleimide (10.8 g, 0.11 mole) were stirred in a RBF at 60° C. After conversion to N-substituted maleamic acid product, acetic anhydride (15.3 g, 0.15 mole) was added. The mixture was stirred for additional time. The product was taken up in organic solvent (DCM) and washed subsequently with sodium bicarbonate and brine, twice each. Finally, the organic layer was dried with magnesium sulfate and the solvent was removed under reduced pressure. FIG. 13 illustrates this synthesis method and FIG. 14 illustrates the reaction mechanism for the transesterification and dehydration-cyclization conversion of the fatty alcohol having a primary amine to the N-substituted maleimide monomer.

Example 7

This example demonstrates free-radical copolymerization of maleate (FIG. 15, left) and maleimide monomers (FIG. 15, right) with styrene. However, the reaction can be customized to synthesize other types of copolymers besides styrene (e.g., olefins, methacrylates, acrylates, styrenes, acrylamides, acrylonitriles, etc.), as discussed above.

Soy maleate (6 g, 0.0136 moles) and styrene (1.42 g, 0.0136 moles) were dissolved in 15 mL of dry toluene in a 50 mL RBF. Benzoyl peroxide (96 mg, 0.4 mmole) was added. The RBF was sealed and purged with nitrogen for 20 minutes. After purging, the RBF was placed in a 100° C. oil bath for 16 hours. The polymer was precipitated in cold methanol three times and dried under vacuum overnight.

It should also be understood that aspects of the various embodiments may be interchanged either wholly or in part. Moreover, those of ordinary skill in the art will appreciate that the foregoing description is by way of example only, and is not intended to limit the disclosure as outline in the appended claims.

The invention claimed is:

1. A monomeric compound comprising:

wherein n is 1, 2, 3, or 4, wherein $R_1$ is hydrogen, a methyl group, an ethyl group, a propyl group, or a butyl group, and wherein $R_2$ is an aliphatic chain from a fatty acid.

2. The monomeric compound of claim 1, wherein $R_2$ is a fatty acid derived from soybean oil, sunflower oil, safflower oil, rapeseed oil, olive oil, peanut oil, or a combination thereof.

3. The monomeric compound of claim 1, wherein the compound is and wherein n=1.

4. The monomeric compound of claim 3, wherein the compound is:

5. The monomeric compound of claim 3, wherein the compound is:

6. The monomeric compound of claim 3, wherein the compound is:

7. The monomeric compound of claim 3, wherein the compound is:

8. The monomeric compound of claim 1, wherein $R_2$ is a linoleic acid chain, a linolenic acid chain, a stearic acid chain, or a palmitic acid chain.

9. The compound of claim 1, wherein $R_1$ is hydrogen.

10. The compound of claim 1, wherein $R_1$ is a methyl group.

11. A method for synthesizing an N-substituted maleimide monomer comprising:
converting a triglyceride to a fatty acid chain having a primary amine group using a base-catalyzed transesterification; and
producing the N-substituted maleimide monomer by dehydration-cyclization conversion of the fatty acid chain having the primary amine group, wherein the N-substituted maleimide monomer has the following structure:

wherein n is 1, 2, 3, or 4,
wherein $R_1$ is hydrogen, a methyl group, an ethyl group, a propyl group, or a butyl group,
and wherein $R_2$ is an aliphatic chain from a fatty acid.

12. The method of claim 11, wherein the fatty acid chain having the primary amine group is prepared by contacting the triglyceride with ethylenediamine, propylenediamine, butylenediamine, or a combination thereof.

* * * * *